United States Patent [19]

Feinberg et al.

[11] Patent Number: 4,894,315
[45] Date of Patent: Jan. 16, 1990

[54] PROCESS FOR MAKING FLEXOGRAPHIC PRINTING PLATES WITH INCREASED FLEXIBILITY

[75] Inventors: Bernard Feinberg, Englishtown; Michael Fryd, Moorestown, both of N.J.; Ernst Leberzammer, Glen Mills, Pa.

[73] Assignee: E. I. Du Pont de Nemours and Company, Wilmington, Del.

[21] Appl. No.: 238,105

[22] Filed: Aug. 30, 1988

[51] Int. Cl.$^4$ .................... G03C 1/68; G03C 7/00
[52] U.S. Cl. .................... 430/281; 430/287; 430/288; 430/300; 430/302; 430/306; 430/325
[58] Field of Search ............... 430/281, 286, 287, 300, 430/302, 325, 288, 306

[56] References Cited

U.S. PATENT DOCUMENTS

| | | | |
|---|---|---|---|
| 4,045,231 | 8/1977 | Toda et al. | 430/286 |
| 4,162,919 | 7/1979 | Richter et al. | 430/286 |
| 4,264,705 | 4/1981 | Allen | 430/271 |
| 4,323,636 | 4/1982 | Chen | 430/271 |
| 4,323,637 | 4/1982 | Chen et al. | 430/271 |
| 4,357,413 | 11/1982 | Cohen et al. | 430/253 |

FOREIGN PATENT DOCUMENTS

| | | | |
|---|---|---|---|
| 263301 | 4/1988 | European Pat. Off. | |
| 266069 | 5/1988 | European Pat. Off. | 1/68 |

OTHER PUBLICATIONS

Handbook of Adhesives, 2nd ed., pp. 304–307 (1977).
Shell booklet (1983) pertaining to Kraton ® Thermoplastic Rubber.

Primary Examiner—Paul R. Michl
Assistant Examiner—C. D. RoDee

[57] ABSTRACT

This invention relates to a process for making a printing relief from a flexographic photosensitive element comprising:
(a) imagewise exposing to actinic radiation a layer of a photosensitive composition, said photosensitive composition comprising a binder having thermoplastic and elastomeric domains, a first addition polymerizable, ethylenically unsaturated monomer having some compatibility with both domains of the binder, and an addition polymerization initiator or initiating system;
(b) removing the unexposed portions; and
(c) applying post development treatment; wherein the improvement comprises increasing the flexibility of the flexographic printing relief by adding at least one additional ethylenically unsaturated monomer so that the ratio of first monomer to the additional monomer is in the range 1:4 to 4:1 based on total weight of monomer, said additional monomer is added to the photosensitive composition prior to imagewise exposing the layer provided that said additional monomer is substantially incompatible with the elastomeric domain of the binder.

11 Claims, No Drawings

PROCESS FOR MAKING FLEXOGRAPHIC PRINTING PLATES WITH INCREASED FLEXIBILITY

FIELD OF THE INVENTION

This invention relates to a process for making flexographic printing plates and, more particularly, to a process for making these plates so that the plates have increased flexibility without adversely affecting other properties such as photospeed and adhesion.

BACKGROUND OF THE INVENTION

Flexographic printing, with photopolymer plates is conducted in the following manner: the photosensitive layer of the flexographic element is imagewise exposed using ultraviolet radiation. Unexposed areas are washed off using a suitable solvent. Solvent is removed by evaporation and, if necessary, the surface is treated to remove tack. The plate is mounted on press using a pressure-sensitive double-coated adhesive tape which is wrapped around and affixed to the plate cylinder. Then the plate is wrapped around and affixed to the outer surface of the tape in intimate contact with the adhesive. If the plate is not sufficiently flexible, the plate will tend to separate, i.e., delaminate, from the adhesive causing poor printing and can completely separate from the plate cylinder to preclude printing. Thus, it is important that the plate be flexible enough so that it remains wrapped around and affixed to the cylinder.

A variety of photopolymerizable compositions, having varying degrees of toughness, have been used to make flexographic printing plates. These compositions can be categorized according to the type of solvent in which they are developed, i.e., either organic solvent soluble or water soluble and they usually comprise (1) an addition polymerizable, nongaseous ethylenically unsaturated monomer, (2) a photoinitiator or photoinitiating system activated by actinic radiation and 3) a thermoplastic, elastomeric polymeric binder comprising polymerized conjugated diene monomers. Photopolymerizable layers are taught in Plambeck, U.S. Pat. No. 2,760,863, Chen et al. U.S. Pat. No. 4,323,636, Toda et al., U.S. Pat. No. 4,045,231; Heinz et al., U.S. Pat. No. 4,320,188. These compositions all suffer from the same defect, namely, they do not impart a sufficient degree of flexibility to plates made from these compositions. Plates made from these photosensitive compositions have a tendency to unwrap from the cylinder to which they are affixed.

U.S. Pat. No. 4,323,636 teaches a photosensitive composition having a solvent-soluble, thermoplastic elastomeric block copolymer to provide photosensitive solvent soluble elements which are useful for making flexographic printing reliefs for letter press printing. Those block copolymers have at least two thermoplastic, nonelastomeric polymer blocks having a glass transition temperature above 25° C. and between said thermoplastic, nonelastomeric blocks, an elastomeric polymer block having a glass transition temperature below 10° C. It is also taught that the monomer should be compatible with either block of the copolymer, and preferably the elastomeric block, in order to secure an essentially non-light scattering mixture. Other photopolymerizable compositions containing elastomeric block copolymers useful for preparing flexographic relief printing plates are taught in U.S. Pat. Nos. 4,430,417 and 4,045,231.

Photopolymerizable elements and processes for their use in preparing relief printing plates are well known in the art: U.S. Pat. No. 2,760,863, U.S. Pat. No. 3,556,791, U.S. Pat. No. 3,798,035, U.S. Pat. No. 3,825,430 and U.S. Pat. No. 3,951,657.

SUMMARY OF THE INVENTION

This invention relates to a process for making a printing relief from a flexographic photosensitive element comprising:

(a) imagewise exposing to actinic radiation a layer of a photosensitive composition, said photosensitive composition comprising a binder having thermoplastic and elastomeric domains, a first addition polymerizable, ethylenically unsaturated monomer having some compatibility with both domains of the binder, and an addition polymerization initiator or initiating system;

(b) removing the unexposed portions; and (c) applying post development treatment; wherein the improvement comprises increasing the flexibility of the flexographic printing relief by adding at least one additional ethylenically unsaturated monomer so that the ratio of first monomer to the additional monomer is in the range 1:4 to 4:1 based on total weight of monomer, said additional monomer is added to the photosensitive composition prior to imagewise exposing the layer provided that said additional monomer is substantially incompatible with the elastomeric domain of the binder.

In another aspect, this invention also relates to a flexographic photosensitive element comprising, inter alia, an additional ethylenically unsaturated monomer which is substantially incompatible with the elastomeric domain of the binder.

DETAILED DESCRIPTION OF THE INVENTION

Binders suitable for use in this invention have two domains--an elastomeric domain and a thermoplastic domain. These binders can be solvent soluble or aqueous or semi-aqueous processible. Any block copolymer is suitable for practicing this invention as long as it has the requisite domain structure. The block copolymers discussed in U.S. Pat. Nos. 4,323,636, 4,430,417 and 4,045,231, all of which are hereby incorporated by reference, can be used. The Kraton ® family of triblock copolymers manufactured by the Shell Chemical Company are also suitable for practicing this invention. The Kraton ® triblock copolymers have an elastomeric block in the center and a thermoplastic block on each end. These triblock copolymers can be divided into three basic types of polymers: polystyrenepolybutadiene-polystyrene (S-B-S), polystyrene-polyisoprenepolystyrene (S-I-S), or polystyrene-poly(ethylenebutylene)polystyrene (S-B-S). The preferred tri-block copolymer is the S-B-S triblock.

The term binder, as used herein, encompasses core shell microgels having an elastomeric crosslinked core and a thermoplastic noncrosslinked shell. Thus, a binder including a blend of a preformed macromolecular polymer and a core shell microgel or a binder consisting entirely of a core shell microgel having an elastomeric core and a thermoplastic shell can be used. For example, the microgels disclosed in U.S. 4,726,877 would not be suitable for practicing this invention because those microgels do not have an elastomeric core and a thermoplastic non-crosslinked shell. The term microgel includes crosslinked spherical polymer molecules of high molecular weight such as of the order of $10^9$ to $10^{10}$ with a particle size of 0.01 to 1.0 micron in diameter prepared by emulsion polymerization. Preferably, the core shell microgel used has less than 10% crosslinking in the core and the shell is not crosslinked.

Core shell microgels can be made from a wide variety of starting materials. Conventionally, monoethylenically unsaturated monomers are used in preparing the bulk portion of the microgel, whereas the crosslinking agents contain at least two double bonds.

Suitable monomers are esters of acrylic and methacrylic acid with $C_1$–$C_{18}$ alcohols. There can be mentioned methyl methacrylate, ethyl acrylate, methacrylic acid, butyl methacrylate, ethyl methacrylate, glycidyl methacrylate, styrene and allyl methacrylate, while other useful monomers include acrylonitrile, methacrylonitrile, acrylic acid, butadiene and 2-ethyl-hexyl acrylate. The preferred monomer for making the core is 2-ethyl-hexyl acrylate.

Other suitable monomers include vinyl ethers and vinyl esters, nitriles and amides of acrylic and methacrylic acid.

A preferred crosslinking agent is butanediol diacrylate (BDDA); while others include ethylene glycol dimethacrylate, tetramethylene glycol diacrylate, trimethylol propane triacrylate, tetraethylene glycol dimethacrylate, methylene bisacrylamide, methylene bismethacrylamide, divinyl benzene, vinyl methacrylate, vinyl crotonate, vinyl acrylate, vinyl acetylene, trivinyl benzene, glycerine trimethacrylate, pentaerythritol tetramethacrylate, triallyl cyanurate, divinyl acetylene, divinyl ethane, divinyl sulfide, divinyl sulfone, dienes such as butadiene, hexatriene, triethylene glycol dimethacrylate, diallyl cyanamide, glycol diacrylate, ethylene glycol divinyl ether, diallylphthalate, divinyl dimethyl silane, glycerol trivinyl ether and the like.

Crosslinking is controlled during manufacture. Thus, core shell microgels having cores with less than 10% crosslinking are prepared by using 10% or less of the crosslinking agent to crosslink the core, i.e., no crosslinking agent is used to make the shell.

Conventionally one or more monomers and crosslinking agents are dispersed in water with suitable emulsifiers and initiators in manufacture of the microgel. Conventional anionic, cationic or nonionic emulsifiers and water soluble initiators can be employed. Examples of emulsifying agents are sodium lauryl sulfate, lauryl pyridine chloride, polyoxyethylene, polyoxypropylene, colloidal silica, anionic organic phosphates, magnesium montmorillonite, the reaction product of 12 to 13 moles of ethylene oxide with 1 mole of octyl phenol, secondary sodium alkyl sulfates and mixtures thereof. Usually from 0.25 to 4% of emulsifier based on the total weight of reactants is used. Examples of initiators are potassium persulfate, sodium persulfate, ammonium persulfate, tertiary butyl hydroperoxide, hydrogen peroxide, azo bis(isobutyronitrile), azo bis(isobutyroimidine hydrochloride), various redox (reduction-oxidation) systems such as hydrogen peroxide and ferrous sulfate and well known persulfatebisulfate bisulfate combinations. Usually from 0.05 to 5% by weight of initiator based on the weight of copolymerizable monomers is used.

Microgels suitable for the practice of the present invention can be produced by the technique of emulsion polymerization as described in U.S. Pat. No. 3,895,082 (Also, British Pat. No. 967,051 teaches a suitable method.) This technique can also be modified by beginning the reaction with one set of monomers and by varying the ratios for the final part of the reaction in order to produce spherical microgels in which the part of the polymer, i.e., the core is a different monomeric composition than the outer part of the polymer, i.e., shell. It is also possible to design the shell for aqueous processibility if organic solvent processibility is not desired. This is done by constructing the shell so that it contains an acid modified copolymer. For the present invention, it is desired that the glass transition temperature of the shell be above 10° C. and the glass transition temperature of the core should be below 25° C. Thus, the core can be characterized as elastomeric while the shell can be characterized as thermoplastic.

The art of emulsion polymerization is well known concerning reaction conditions to produce spherical microgels dispersed in a water phase. Unless the dispersion can be used as made and contain no objectionable impurities or byproducts, it is usually necessary to convert the microgels to a solid prior to their use as a photosensitive composition. Well-known techniques of coagulation, filtration, washing and drying may be employed for this purpose. Freeze drying is a particularly useful method for the present invention. Generally the amount of crosslinking agent in the microgel will be less than 20% by weight of the overall weight of the microgel and, preferably, less than 10% by weight.

The weight ratio of the core to the shell is usually in the range from about 4:1 to about 1:4.

Suitable preformed macromolecular polymers include the following: polyacrylate and alpha-alkyl polyacrylate esters, e.g., polymethyl methacrylate and polyethyl methacrylate; polyvinyl esters, e.g. polyvinyl acetate, polyvinyl acetate/acrylate, polyvinyl acetate/methacrylate and hydrolyzed polyvinyl acetate; ethylene/vinyl acetate copolymers; polystyrene polymers and copolymers, e.g. with maleic anhydride and esters; vinylidene chloride copolymers, e.g. vinylidene chloride/acrylonitrile; vinylidene chloride/methacrylate and vinylidene chloride/vinyl acetate copolymers; polyvinyl chloride and copolymers, e.g., polyvinyl chloride/acetate; saturated and unsaturated polyurethanes; synthetic rubbers, e.g. butadiene/acrylonitrile, acrylonitrile/butadiene/styrene, methacrylate/acrylonitrile/butadiene/styrene copolymers, 2chlorobutadiene-1,3-polymers, chlorinated rubber, and styrene/butadiene/styrene, styrene/isoprene/styrene block copolymers; high molecular weight polyethylene oxides of polyglycols having average molecular weights from about 4,000 to 1,000,000, epoxides, e.g. epoxides containing acrylate or methacrylate groups; copolyesters, e.g., those prepared from the reaction product of a polymethylene glycol of the formula $HO(CH_2)_nOH$, where n is a whole number from 2 to 10 inclusive, ad (1) hexahydroterephthalic, sebacic and terephthalic acids, (2) terephthalic, isophthalic and sebacic acids, (3) terephthalic and sebacic acids, (4) terephthalic and isophthalic acids and (5) mixtures of copolyesters prepared from said glycols and (i) terephthalic, isophthalic and sebacic acids and (ii) terephthalic, isophthalic, sebacic and adipic acids; nylons or polyamides, e.g., N-methoxymethyl polyhexamethylene adipamide; cellulose esters, e.g., cellulose acetate, cellulose acetate succinate and cellulose acetate butyrate; cellulose ethers, e.g., methyl cellulose, ethyl cellulose and benzyl cellulose; polycarbonates; polyvinyl acetal, e.g. polyvinyl butyral, polyvinyl formal; polyformaldehydes.

In the case where aqueous development of the photosensitive composition is desirable, the binder should contain sufficient acidic or other groups to render the composition processible in aqueous developer. Useful aqueousprocessible binders include those disclosed in U.S. Pat. Nos. 3,458,311 and 4,273,857. Useful amphoteric polymers include interpolymers derived from N-alkylacrylamides or methacrylamides, acidic film-forming comonomer and an alkyl or hydroxyalkyl acrylate such as those disclosed in U.S. Pat. No. 4,293,635.

The binder is present in at least 35% by weight of the photosensitive composition.

By compatibility is meant the ability of two or more constituents to remain dispersed with one another without causing appreciable scattering of actinic radiation.

The selection of an appropriate monomer as the first monomer or the additional monomer is determined by using the compatibility test described in Example 1. A similar test is described in the Handbook of Adhesives, 2d Ed., page 307, I. Skeist (ed.), Van Nostrand Reinhold Co. (1977), which is hereby incorporated by reference. Both the test described in Example 1 and the Handbook of Adhesives compatibility test determine qualitatively with which domain a given monomer is compatible. Clarity of the dried film indicates mutual solubility. Haze indicates some compatibility. An opaque film indicates substantial incompatibility.

U.S. Pat. No. 4,323,636, discussed above, teaches that an essentially non-light scattering mixture can be secured when the ethylenically unsaturated monomer is compatible with either block of the block copolymers used in the binder. It does not teach how to obtain a more flexible printing element having a sufficient degree of flexibility to remain affixed to the small cylinders often used for printing in the packaging industry.

Surprisingly and unexpectedly, it has been discovered that a more flexible flexographic printing plate can be obtained, without adversely affecting other properties such as photospeed, resistance to cold flow, etc., by using a mixture of a first monomer which is compatible with both domains of the binder and at least one additional monomer which is substantially incompatible with the elastomeric domain of the binder. The ratio of the first monomer to the additional monomer is usually in the range 1:4 to 4:1.

This discovery is surprising and unexpected because the additional monomers mentioned herein are known to produce hard polymers and, thus, were expected to reduce the flexibility of the printing plate.

In addition to the compatibility test described above and in Example 1, it is possible to determine compatibility by evaluating in which domain the monomer has distributed predominantly by using any one of three techniques: thermomechanical analysis (TMS), dynamic mechanical analysis (DMA), or differential scanning calorimetry (DSC). These techniques explore different polymer properties in order to identify discrete domains by their glass transition temperatures. DSC explores heat capacity of a polymer. TMA explores free volume of a polymer above its glass transition temperature. DMA explores changes in the modulus of a polymer.

When a monomer has distributed substantially in a given domain, a depression of the glass transition temperature should be observed. In the case of the first monomer, it is believed that both domains of the binder should be affected. Thus, a depression of the glass transition temperature of both domains should be observed. In the case of the additional monomer, it is believed that the additional monomer is distributed outside the elastomeric domain. The additional monomer is either distributing predominantly in the thermoplastic domain or it is forming its own domain. No glass transition temperature depression should be observed for the elastomeric domain when the additional monomer is evaluated.

It is also possible to estimate whether a monomer will be more compatible with a particular domain of the binder by evaluating the solubility parameters of the monomers relative to the solubility parameters of the binder's domains. The solubility parameter (SP) of a polymer is defined as the same as that of a solvent in which the polymer will mix in (a) all proportions, (b) without heat effect, (c) without volume change, and (d) without reaction or any special association. The solubility parameter is then a measure of the total forces holding the molecules of a solid or a liquid together. The general approach is that materials having the same solubility parameter tend to be miscible. Those with different solubility parameters tend to be mutually insoluble. For example, a Kraton ® polybutadiene midblock, i.e., the elastomeric domain, has a solubility parameter of about 8.4 and the polystyrene domain has a solubility parameter of about 9.1. Monomers which would be compatible with the thermoplastic domain should have solubility parameters of 9.1 or higher. It is probable that if a monomer has a substantially higher solubility parameter than the solubility parameter of the elastomeric domain, it would be substantially incompatible with the elastomeric domain.

Monomers useful as the first addition polymerizable ethylenically unsaturated monomer should be capable of forming a high polymer by free radical initiated chain propogating addition polymerization and can have some compatability with both domains of the binder. There can be mentioned as the first addition polymerizable monomer: unsaturated esters of alcohols, especially such esters of alpha-methylene carboxylic acids and substituted alpha-methylene carboxylic acids, more especially such esters of alkylene polyols, and most especially alkylene polyol di- and tri-acrylates prepared from alkylene polyols of 2-15 carbon atoms, ethylene glycol diacrylate, glycerol diacrylate, glycerol triacrylate, ethylene glycol dimethacrylate, 1,3-propanediol dimethacrylate, 1,2,41,4-benzenediol dimethacrylate, 1,2-benzenedimethanol diacrylate, 1,3-propanediol diacrylate, 1,3-pentanediol dimethacrylate, p-alpha,alpha-dimethylbenzylphenyl acrylate, t-butyl acrylate, N,N-dimethylaminoethyl acrylate, N,Ndiethylaminoethyl methacrylate, 1,4-butanediol diacrylate, 1,6-hexanediol diacrylate, 1,10-decanediol diacrylate, 2,2-dimethylolpropane diacrylate, 1,4-butanediol dimethacrylate, 1,6-hexanediol dimethacrylate, 2,2,4-trimethyl-1,3-pentanediol dimethacrylate, 1-phenylethylene-1,2-dimethacrylate, ethylene glycol acrylate phthalate, and the like. 1,6-Hexanediol diacrylate is the preferred first addition monomer for practicing the process of this invention.

Monomers, suitable as the additional ethylenically unsaturated monomer, should be substantially incompatible with the elastomeric domain of the binder. This can be determined by using any of the techniques described above for selecting the first monomer. If a monomer is substantially incompatible with the elastomeric domain, then it should have a solubility parameter which greatly exceeds the solubility parameter of the elastomeric domain of the binder. It should be understood that solubility parameters are not conclusive as to the final disposition of components in a multiphase system. They merely provide guidance as to the likelihood where a component might be found.

The compatibility test detailed in Example 1 was used to select monomers useful as the additional monomer. Those monomers which reacted with the elastomeric binder solution by producing a substantially opaque film in this test would be substantially incompatible with the elastomeric polybutadiene domain of the binder. As was noted above, constituents which have some incompatibility form hazy mixtures which scatter light. Opaque mixtures which have the highest degree of light scattering indicate substantial incompatibility of the constituents.

The following are illustrative of monomers which were found to be suitable as the additional monomer as determined by the compatibility test: pentaerythritol tetraacrylate (PETA), dipentaerythritol monohydroxy pentaacrylate (DIPETA), highly propoxylated glycerol triacrylate, diacrylate and dimethacrylate esters of diepoxy polyethers derived from aromatic polyhydroxy compounds such as bisphenols, novolaks and similar compounds such as those described by Crary in U.S. Pat. No. 3,661,576. DIPETA is the preferred monomer for use as the additional monomer. It should be understood that the compatibility test described in Example 1 can be run with a multitude of different monomers and binder solutions depending upon the constituents under study. For example, elastomeric binder solutions containing polyisoprene and poly(ethylenebutylene) can be used. The choice depends upon the binder of interest in formulating a photosensitive composition.

It has been found that a ratio of first monomer to additional monomer can range usually from about 1:4 to about 4:1 based on total weight of monomer. Preferably, the ratio of the monomers is about 1:1 or, most preferably, 1:3. Although less desirable, it is possible to work with a formulation having a ratio of first monomer to second monomer of about 3:1. Compositions having all additional monomer and no first monomer are to be avoided because other properties can be adversely affected.

Generally, at least 5% total monomer, i.e., first monomer and additional monomer, is present based on the weight of the photosensitive composition.

It is believed that distribution of the additional monomer outside the elastomeric domain retards crosslinking of the elastomeric domain and is believed to drive plasticizer, if present in the composition, out of the thermoplastic domain of the binder into the elastomeric domain. The surprising and unexpected result obtained by selecting at least one monomer which is incompatible with the elastomeric domain and a monomer which has some compatibility with both domains of the binder in that monomers such as, DIPETA, PETA and highly propoxylated glycerol triacrylate, diacrylate, etc., are expected to drastically reduce the flexibility of plates made from compositions containing these monomers because these monomers produce such hard polymers when photopolymerized. Not only does the resulting plate have increased flexibility, none of the other properties of the printing plate, such as resistance to cold flow, photospeed, adhesion, etc., are adversely affected.

If a plasticizer is used, it should be compatible with the elastomeric domain of the binder. Examples of suitable plasticizers are liquid low molecular weight (MW<5000) polybutadienes and aliphatic hydrocarbon oils. Plasticizer, if used is usually present in at least 5% by weight of the photosensitive composition.

Preferred free radical-generating addition polymerization initiators activatable by actinic light and thermally inactive at and below 185° C. include the substituted or unsubstituted polynuclear quinones which are compounds having two intracyclic carbon atoms in a conjugated carbocyclic ring system, e.g., 9,10-anthraquinone, 1-chloroanthraquinone, 2-chloroanthraquinone, 2-methylanthraquinone, 2-ethylanthraquinone, 2-tert-butylanthraquinone, octamethylanthraquinone, 1,4-naphthoquinone, 9,10-phenanthrenequinone, 1,2-benzanthraquinone, 2,3-benzanthraquinone, 2-methyl-1,4-naphthoquinone, 2,3-dichloronaphthoquinone, 1,4-dimethylanthraquinone, 2,3-dimethylanthraquinone, 2-phenylanthraquinone, 2,3-diphenylanthraquinone, sodium salt of anthraquinone alphasulfonic acid, 3-chloro-2-methylanthraquinone, retenequinone, 7,8,9,10-tetrahydro-naphthacenequinone, and 1,2,3,4-tetrahydrobenz(a)anthracene-7,12-dione. Other photoinitiators which are also useful, even though some may be thermally active at temperatures as low as 85° C., are described in U.S. Pat. No. 2,760,863 and include vicinal ketaldonyl alcohols, such as benzoin, pivaloin, acyloin ethers, e.g., benzoin methyl and ethyl ethers; alpha-hydrocarbon-substituted aromatic acyloins, including alpha-methylbenzoin, alpha-benzoin and alpha-phenylbenzoin. Photoreducible dyes and reducing agents disclosed in U.S. Pat. Nos. 2,850,445; 2,875,047; 3,097,096; 3,074,974; 3,097,097; and 3,145,104, as well as dyes of the phenazine, oxazine, and quinone classes; Michler's ketone, benzophenone, 2,4,5-triphenyl-imidazolyl dimers with hydrogen donors, and mixtures thereof as described in U.S. Pat. Nos. 3,427,161; 3,479,185; and 3,549,367 can be used as initiators. Similarly the cyclohexadienone compounds of U.S. Pat. No. 4,341,860 are useful as initiators. Also useful with photoinitiators and photoinhibitors are sensitizers disclosed in U.S. Pat. No. 4,162,161. Initiators are present in amounts from 0.001% to 10.0% or more based on the weight of the photosensitive composition.

Thermal polymerization inhibitors that can be used in photopolymerizable compositions are: p-methoxyphenol, hydroquinone, and alkyl and aryl-substituted hydroquinones and quinones, tert-butyl catechol, pyrogallol, copper resinate, naphthylamines, beta-naphthol, cuprous chloride, 2,6-di-tertbutyl-p-cresol, phenothiazine, pyridine, nitrobenzene and dinitrobenzene, p-toluquinone and chloranil. Also useful for thermal polymerization inhibitors are the nitroso compositions disclosed in U.S. Pat. No. 4,168,982. Inhibitors are usually present in at least 0.001% by weight of the photosensitive composition.

Suitable base or support materials include metals e.g., steel and aluminum plates, sheets and foils, and films or plates composed of various film-forming synthetic resins or high polymers, such as the addition polymers and in particular vinylidene chloride copolymers with vinyl chloride, vinyl acetate, styrene, isobutylene and acrylonitrile; vinyl chloride homopolymers and copolymers with vinyl acetate, styrene, isobutylene and acrylonitrile; linear condensation polymers such as polyesters, e.g., polyethylene terephthalate, polyamide, e.g., polyhexamethylenesebacamide; polyimides, e.g., films as disclosed in assignee's Edwards, U.S. Pat. No. No. 3,179,634 and polyester amide, e.g., polyhexamethylenedipamide adipate. Fillers or reinforcing agents can be present in the synthetic resin or polymer bases such as the various fibers (synthetic modified, or natural), e.g., cellulosic fibers, for instance, cotton, cellulose acetate, viscose rayon, paper; glass wool; nylon and polyethylene terephthalate. These reinforced bases may be used in laminated form. Various anchor layers disclosed in U.S. Pat. No. 2,760,863 can be used to give strong adherence between the support and the photosensitive layer or, in the case of transparent support, pre-exposure through the support to actinic radiation may be useful. The adhesive compositions disclosed in assignee's Burg, U.S. Pat. No. 3,036,913, are also effective.

A transparent cover sheet such as a thin film of polystyrene, polyethylene, polypropylene or other strippable material is used to prevent contamination of or damage to the photosensitive layer during storage or manipulation. For solvent developable photopolymerizable compositions, a thin hard, flexible, solvent-soluble layer, e.g., a layer of a polyamide, copolymer of polyethylene and polyvinyl acetate, etc., is used on the upper surface of the photosensitive layer to protect for reuse an image-bearing negative or transparency superposed thereon or to improve contact or alignment with the photosensitive surface.

In general, the process of preparing a flexographic printing plate from a photopolymer element includes the steps of main image exposure, development or washout, postdevelopment treatment which includes drying, and postexposure. Detackification is an optional post-development treatment which can be applied if the surface is still tacky.

A backflash exposure may be used with elements having a transparent support. Backflash generally uses a radiation source emitting a principal wavelength around 360 nm. It serves to sensitize the plate and establishes the depth of the plate relief. The backflash procedure gives the photopolymer layer a uniform and relatively short exposure through the support, thereby photocrosslinking binder and monomer in the support region.

Printing reliefs can be made from a photosensitive composition of this invention by exposing to actinic radiation selected portions of a photosensitive layer through an imagebearing transparency. During the addition-polymerization or cross-linking, the ethylenically unsaturated compound composition is converted to the insoluble state in the radiationexposed portions of the layer, with no significant polymerization or cross-linking taking place in the unexposed portions or areas of the layer. The unexposed portions of the layer are removed by means of an organic or aqueous or semi-aqueous solvent. The process transparency may be constructed of any suitable material including cellulose acetate film and oriented polyester film.

Actinic radiation from any source and of any type can be used in the photopolymerization process. The radiation may emanate from point success or be in the form of parallel rays or divergent beams. By using a broad radiation source relatively close to the image-bearing transparency, the radiation passing through the clear areas of the transparency enters as divergent beams and thus irradiates a continually diverging area in the photopolymerizable layer underneath the clear portions of the transparency. This results in a polymeric relief having its greatest width at the bottom of the photopolymerizable layer, i.e., a frustrum, the top surface of the relief being the dimensions of the clear area.

Inasmuch as the free-radical generating systems activatable by actinic radiation generally exhibit their maximum sensitivity in the ultraviolet range, the radiation source should furnish an effective amount of this radiation, preferably having a wavelength range between about 2500A and 5000A. Suitable sources of such radiation, in addition to sunlight, include carbon arcs, mercury-vapor arcs, fluorescent lamps with ultraviolet radiation-emitting phosphors, argon glow lamps, lasers, electron flash units and photographic flood lamps. Electron accelerators and electron beam sources through an appropriate mask may also be used. Of these, the mercury-vapor lamps, particularly the sun lamps, are most suitable.

The radiation exposure time may vary from fractions of a second to minutes, depending upon the intensity and spectral energy distribution of the radiation, its distance from the composition and the nature and amount of the composition available. Customarily, a mercury vapor arc or a sunlamp is used at a distance of about 1.5 to about 60 inches (3.8-163 cm) from the photosensitive composition. Exposure temperatures are preferably operated at about ambient temperatures or slightly higher, i.e., about 20° to about 35° C.

Solvent development may be carried out at about 25° C., but best results are sometimes obtained when the solvent is warm, e.g., 30° to 60° C. Development time can be varied, but it is preferably in the range of about 5 to 25 minutes. Developer may be applied in any convenient manner, including immersion, spraying and brush or roller application. Brushing aids in removing the unpolymerized or non-crosslinked portions of the composition. Washout is frequently carried out in an automatic processing unit which uses solvent and mechanical brushing action to remove the unexposed portions of the plate, leaving a relief constituting the exposed image and floor.

Following solvent development, the relief printing plates are generally blotted or wiped dry, and then dried in a forced air or infrared oven. Drying times and temperatures vary, but drying for 60 to 120 minutes at 60° C. (140° F.) is typical. High temperatures are not recommended as shrinkage of the support may cause registration problems. Additional air drying overnight (16 hours or more) is common. Solvent will continue to evaporate from the printing relief during drying at ambient conditions.

Most flexographic printing plates are uniformly post-exposed to ensure that the photocrosslinking process is complete and that the plate will remain stable during printing and storage. This "post-exposure" utilizes the same ultraviolet radiation source as the main exposure (usually wavelengths of 300 to 420 nm). Post-exposure is used to complete polymerization and maximize plate hardness and durability, but does not remove tackiness. Tackiness can be removed by methods well known in the art such as treatment with bromine solutions, treatment with light at a wavelength below 300 nm, etc.

The primary purpose of each exposure step is to affect polymerization, and actinic radiation from a variety of sources can be used, including commercial ultravioletfluorescent tubes, medium, high and low pressure mercury vapor lamps, argon glow lamps, electronic flash units, photographic flood lamps, pulsed xenon lamps, carbon arc lamps, etc. The radiation source must emit an effective amount of radiation having a wavelength in the range of 230 nm to 450 nm, preferably 300 to 420 nm, and more preferably, 340 to 400 nm. For efficient photopolymerization, the wavelength is matched to the absorption characteristics of the photoinitiator present in the photopolymerizable layers. A standard radiation source is the Sylvania 350 Blacklight fluorescent lamp (FR 48T12/350 VL/VHO/180, 115w) which emits actinic radiation having a central wavelength around 354 nm. Exposure times vary from a few seconds to a few minutes, depending on the output of the lamps, distance from the lamps, relief depth desired, and the thickness of the plate.

The following examples illustrate the practice of the invention:

EXAMPLE 1

Determination of compatibility of monomers with polymers 1,6-Hexanediol diacrylate (HMDA) (1), isodecyl acrylate (2), C-14 diacrylate (3), propoxylated neopentyl glycol acrylate (4), highly propoxylated glycerol triacrylate (HPGT) (5) pentaerythritol monohydroxy pentaacrylate (6) and diacrylate ester of bisphenol A epoxy resin derived from bisphenol A and epichlorohydrin (DAE) (7) were tested for compatibility in different polymers according to the following procedure:

A thermoplastic binder solutions (B2) was made by dissolving 20 g of polystyrene (Aldrich Chemical Co.) in 200 g methylene chloride. An elastomeric binder solution (B1) was made by dissolving 20g cis-1,4-polybutadiene (Firestone Co.) in 200 g methylene chloride. Bidner solution (B3) was made by dissolving 20 g of Kraton® 1102 in 200 g methylene chloride. Kraton® 1102 is a S-B-S triblock polymer manufactured by the Shell Chemical Company.

0.5 g of each monomer was added to 20 g of each binder solution. Each solution was clear.

A small amount of each solution was poured onto a 6"×6" Mylar® square so that it occupied about half of the Mylar® square. The solutions were allowed to dry on each square. A film formed on the surface. The entire series of solutions was examined. The type of film formed was characterized as clear/transparent, cloudy/hazy or substantially opaque.

Monomers which were compatible with the polymer produced a clear film on the Mylar® surface. Monomers which had some compatibility produced a hazy film and monomers which were incompatible produced an essentially opaque film. According to the results presented below HMDA, isodecyl acrylate, C-14 diacrylate and propoxylated neopentyl glycol diacrylate had some compatibility with all three binder solutions. Thus, they would be useful as the first monomer.

Monomers useful as the additional monomer formed essentially opaque or cloudy-opaque films on the Mylar® surface when combined with the elastomeric (B1) binder solution. Highly propoxylated glycerol triacrylate, DIPETA and diacrylate ester of bisphenol A epoxy resin derived from bisphenol A and epichlorohydrin were substantially incompatible with the elastomeric (B1) binder solution. The results are presented in Table 1.

TABLE 1

| Binder | Monomer | | | | | | |
|---|---|---|---|---|---|---|---|
| Solution | 1 | 2 | 3 | 4 | 5 | 6 | 7 |
| B1 | P | C | C | P | X | X | X |
| B2 | C | C | C | C | X | X | P |

TABLE 1-continued

| Binder | Monomer | | | | | | |
|---|---|---|---|---|---|---|---|
| Solution | 1 | 2 | 3 | 4 | 5 | 6 | 7 |
| B3 | C | C | C | C | X | P-X | C |

C = clear, transparent
P = cloudy, hazy
X = essentially opaque

EXAMPLE 2

580 g of methylene chloride, 53.2 g 1,1,1,-dimethoxyphenylacetophenone, 26.6 g butylated hydroxyltoluene and 6.4 g of dye solution were mixed together at room temperature to produce a master batch. The dye solution consisted of 2.56% red dye Cl109 in hydroxyethyl methacrylate.

25 g master batch, 58.5 g Kraton® 1102, and the amounts of DIPETA, HMDA and plasticizer listed in Table 2 were stirred together by hand and allowed to stand overnight. The plasticizer was a mixture of equal amounts by weight of two liquid polybutadienes—a cis 1,4-polybutadiene (Huls, W. Germany) and a 1,2-polybutadiene (Nippon Soda Company, Japan).

All amounts are in grams unless otherwise indicated.

TABLE 2

| | Plate | | | | |
|---|---|---|---|---|---|
| Components | A | B | C | D | E |
| DIPETA[2] | 10.0 | 7.5 | 5.0 | 2.5 | 0.0 |
| HMDA[1] | 0.0 | 2.5 | 5.0 | 7.5 | 10.0 |
| Plasticizer | 28.5 | 28.5 | 28.5 | 28.5 | 28.5 |

[1] = used as first monomer
[2] = used as additional monomer

The next day this mixture was milled for fifteen minutes at 120° to 130° C. on a two roll mill.

About 95 g milled polymer was placed into a 6"×9"×0.117" mold. The polymer was then sandwiched between two pieces of polyester which constituted the support and the cover sheet. The coversheet had a tin (0.0002") release layer (a polyamide hot melt adhesive compound manufactured by Henkel Company) coated on it. This was pressed between heated platens at about 140° C. for three minutes at minimum contact, 2 minutes at 5000 psi and 1 minute at 10,000 psi.

EXAMPLE 3

25 g master batch, which was made as set forth in Example 2, 58.5 g Kraton® 1102, 28.5 g low molecular weight polybutadiene plasticizer, and the amounts of the monomers noted below were stirred together by hand and allowed to stand.

| Monomer | Plate F | Plate G |
|---|---|---|
| C-14 diacrylate[1] | 5.0 | 10.0 |
| HPGT[2] | 5.0 | 0.0 |

[1] = used as first monomer
[2] = used as additional monomer

Photosensitive plates were prepared according to the procedure outlined in Example 2 above.

EXAMPLE 4

Test for Flexibility of Printing Plates

Plates A-G, having dimensions of 1¼"×9", were exposed for 2 minutes through the back and 18 minutes through the front using a bank of Sylvania 350 Blacklight fluorescent lamps (FR 48T12/350 VL/VHO/180, 15 w). The plates were allowed to stand flat for 30 minutes. Then, the plates were placed in a holder mounted on the edge of a table so that seven inches of the the plate hung over the edge of the table. A perpendicular line was drawn from the bottom of plate hanging over the edge to the table. The flexibility of the plate was expressed as the distance (in mm) of the perpendicular to the top of the table. Generally, the higher the distance of the perpendicular to the top of the table, the greater the flexibility. The data presented in Table 3 show that the more additional monomer present, the more flexible the plate. However, while Plate A, which contained only DIPETA, had the most flexibility, plates having all additional monomer had poor photospeed. (See data in Example 6.)

The data obtained from the flexibility test were confirmed by the Shore A hardness results which are set forth in Table 3.

TABLE 3

| Plate | Monomers HMDA[1] (g) | DIPETA[2] (g) | Flexibility (mm) | Shore A Hardness Exposed |
|---|---|---|---|---|
| A | 0 | 10 | 95 | 53 |
| B | 2.5 | 7.5 | 84 | 55 |
| C | 5.0 | 5.0 | 87 | 58 |
| D | 7.5 | 2.5 | 83 | 58 |
| E | 10 | 0 | 72 | 62 |
| F | 0[3] | 0[3] | 93 | 56 |
| G | 0[3] | 0[3] | 86 | 60 |

[1] = First monomer
[2] = Additional monomer
[3] = See Example 3

EXAMPLES

Plates H-O were made according to the procedure described in Example 2 except that the monomers used were varied. The monomers used are set forth in Table 4. All amounts are in grams unless otherwise indicated.

Plates H-O were tested for flexibility according to the procedure described in Example 4. Flexibility data are set forth in Table 4.

TABLE 4

| | Monomer (grams) | | | | | |
|---|---|---|---|---|---|---|
| | First Monomer | | Additional Monomer | | | Flexibility |
| Plate | HMDA | C-14 diacrylate | DIPETA | HPGT | DAE | (mm) |
| H | 0 | 0 | 10 | 0 | 0 | 99 |
| I | 0 | 5 | 5 | 0 | 0 | 90 |
| J | 0 | 10 | 0 | 0 | 0 | 73 |
| K | 10 | 0 | 0 | 0 | 0 | 72 |
| L | 5 | 0 | 0 | 5 | 0 | 81 |

TABLE 4-continued

| | Monomer (grams) | | | | | |
|---|---|---|---|---|---|---|
| | First Monomer | | Additional Monomer | | | Flexibility |
| Plate | HMDA | C-14 diacrylate | DIPETA | HPGT | DAE | (mm) |
| M | 0 | 0 | 0 | 10 | 0 | 85 |
| N | 0 | 0 | 0 | 0 | 10 | 101 |
| O | 5 | 0 | 0 | 0 | 5 | 85 |

These results show that the flexibility of a plate containing a first monomer increases when additional monomer is also present. Plates J and K contained all first monomer and flexibility readings of 73 and 72 resectively. Plates I, L and O contained 1:1 ratios of first and additional monomers. A noticeable improvement in flexibility was observed. The results were 90, 81, and 85, respectively. What is so surprising is that the monomers used as additional monomers are known to give hard plates, yet, the results show an increase in flexibility of plates containing a mixture of monomers.

EXAMPLE 6

Another series of plates were made and tested for flexibility, adhesion and photospeed.

50 g master batch which was made as described in Example 2, 117 g Kraton® 1102 and 57 g plasticizer, also described in Example 2, and amounts of the monomers set forth in Table 5 were stirred together by hand and allowed to stand. All amounts are in grams.

Plates 1-8 were prepared according to the procedure described in Example 2. These plates, having dimensions 1¼"×9" were exposed for 2 minutes through the back and 18 minutes through the front using a bank of Sylvania 350 Blacklight fluorescent lamps (FR 48T12/350 VL/VHO/180, 115w).

Plates 1 and 8 contained all additional monomer. Plates 5 and 7 contained all first monomer. Plates 2, 3, 4 and 6 contained mixtures of first and additional monomer

Adhesion Test

Adhesion of photopolymer to polyester support is important because the photopolymer will separate from the polyester support if adhesion is too low. Major problems result if this occurs during printing. The adhesion of photopolymers used in Plates 1 to 8 was measured on an Instron Tensile Tester by peeling a one inch wide strip at ten inches per minute. The sample configuration was a "T-peel". Results are expressed in pounds per inch of sample. Adhesion test results are set forth in Table 5. Plates with less than 5 pounds per inch of plate adhesion did not adhere properly to the polyester support.

TABLE 5

| Plate | First Monomer[c] HMDA | C-14 diacrylate | Additional Monomer[c] HPGT | DIPETA | Flexibility[a] (mm) | Shore A Hardness Exposed | Adhesion (lbs/in) of Plate) |
|---|---|---|---|---|---|---|---|
| 1 | 0 | 0 | 0 | 20 | 103 | 50 | 20 |
| 2 | 5 | 0 | 0 | 15 | 95 | 53 | 16 |
| 3 | 10 | 0 | 0 | 10 | 83 | 58 | 100[b] |
| 4 | 15 | 0 | 0 | 5 | 82 | 62 | 2.0 |
| 5 | 20 | 0 | 0 | 0 | 64 | 64 | 0.8 |
| 6 | 0 | 10 | 10 | 0 | 75 | 59 | 0.1 |
| 7 | 0 | 20 | 0 | 0 | 80 | 62 | 0.1 |

TABLE 5-continued

| Plate | First Monomer[c] HMDA | C-14 diacrylate | Additional Monomer[c] HPGT | DIPETA | Flexibility[a] (mm) | Shore A Hardness Exposed | Adhesion (lbs/in) of Plate) |
|---|---|---|---|---|---|---|---|
| 8 | 0 | 0 | 20 | 0 | 95 | 55 | 0.3 |

[a]Flexibility data was obtained according to the procedure described in Example 4.
[b]This number indicates that the bond between the photopolymer and the support was stronger than the bonds holding the photopolymer together.
[c]Amounts are in grams.

The results in Table 5 show that the plates 1, 2 and 3 had the best adhesion. Plate 1 contained all DIPETA. Plates 2 and 3 contained DIPETA and HMDA in the amount set forth in Table 5. Plates 1-3 also had good flexibility and Shore A hardness readings.

EXAMPLE 7

Photospeed Test

The relative photospeed of the plates 1-8 was determined by examining (1) the back exposure time required to achieve a floor depth of 75 mils, (2) the exposure time required to hold the image detail represented by a 7 mil line and (3) the exposure time required to hold a 2% highlight dot. The light exposure source used was the same as described in Example 4.

To determine the back exposure time, the plates were exposed through the transparent support such that different segments of each plate were exposed for 0, 30, 60, 90, 120, and 150 seconds. The plates were then developed by washing with Cyrel ® Washout Solvent for 5 minutes and dried for 1 hour. The depth of the plate floor developed at each exposure time was measured. The time required to achieve a floor depth of 75 mils was the back exposure time.

A main exposure test was used to determine the exposure time to hold a 7 mil line and a 2% highlight dot. Raw plates were first backexposed overall for the length of time determined above. The coversheet was then removed and the plate was exposed through a test negative such that one area of the plate was exposed imagewise through the negative for 5 minutes, a second area was exposed through the negative for 10 minutes, and a third area was exposed through the negative for 20 minutes. The plates were developed as described above. The exposure times were the minimum time required to hold a 7 mil line straight and the minimum time required to hold the 2% highlight dot on a 120 lines per inch screen with no dropouts.

The results, given in Table 6, show that the photospeed was about the same with the blend of two monomers as with the first monomer alone, i.e., the presence of the additional monomer did not adversely affect photospeed. Only in the case where the additional monomer was the only monomer (sample Plates 1 and 8) was the photospeed unacceptable.

TABLE 6

| Plate | Back Exposure (seconds) | Exposure Times (minutes) 7 mil line | 2% dot |
|---|---|---|---|
| 1 | 180 | 20 | (3) |
| 2 | 180 | 5 | 20 |
| 3 | 160 | 5 | 10 |
| 4 | 120 | 5-10 | 10 |
| 5 | 120 | 5 | 10 |
| 6 | 160 | 10 | 10 |
| 7 | 180 | 5 | 20 |
| 8 | 180 | 20 | (3) |

(3) = The 2% highlight dots were not held with any exposure.

What is claimed is:

1. In a process for making a printing relief from a flexographic photosensitive element comprising:
   (a) imagewise exposing to actinic radiation a layer of a photosensitive composition, said photosensitive composition comprising a binder having thermoplastic and elastomeric domains, a first addition polymerizable, ethylenically unsaturated monomer having some compatibility with both domains of the binder and an addition polymerization initiator or initiating system;
   (b) removing the unexposed portions; and
   (c) applying post development treatment; wherein the improvement comprises increasing the flexibility of the flexographic printing relief by adding at least one additional ethylenically unsaturated monomer which produces a hard polymer when photopolymerized, said monomer being substantially incompatible with the elastomeric domain of the binder, the ratio of first monomer to the additional monomer is in the range 1:4 to 4:1 based on total weight of monomer, and said additional monomer is added to the photosensitive composition prior to imagewise exposing the layer.

2. The process according to claim 1 wherein the binder is a styrene-butadiene-styrene block copolymer, the first monomer is 1,6-hexanediol diacrylate and the additional monomer is dipentaerythritol monohydroxy pentacrylate.

3. The process according to claim 1 wherein the binder is a blend of a preformed macromolecular binder and a core shell microgel having a crosslinked core and a noncrosslinked shell.

4. The process according to claim 1 wherein the compatibility test is used to determine the incompatibility of the additional monomer with the elastomeric domain.

5. A flexographic photosensitive element which comprises a support; a layer of a photosensitive composition; said composition comprising:
   (a) a binder having thermoplastic and elastomeric domains;
   (b) an initiator or initiating system activated by actinic radiation;
   (c) a first addition polymerizable ethylenically unsaturated monomer having some compatibility with both domains of the binder; and
   (d) at least one additional addition polymerizable ethylenically unsaturated monomer wherein the ratio of the first monomer to the second monomer is in the range 1:4 to 4:1 based on total weight of monomer, said additional monomer is substantially incompatible with the elastomeric domain of the binder; and a flexible cover sheet.

6. An element according to claim 5 wherein the binder is a styrene-butadiene-styrene block copolymer, the first monomer is 1,6 hexanediol diacrylate and the additional monomer is dipentaerythritol monohydroxy pentacrylate.

7. An element according to claim 5 wherein the binder is a blend of a prefomed macromolecular binder and a core shell microgel having a crosslinked core and a noncrosslinked outer shell.

8. An element according to claim 5 wherein the additional monomer is selected from the group consisting of highly propoxylated glycerol triacrylate, pentaerythritol monohydroxy pentaacrylate and diacrylate ester of bisphenol A epoxy resin derived from bisphenol A and epichlorohydrin.

9. An element according to claim 5 wherein the photosensitive layer also has a plasticizer.

10. An element according to claim 5 where the compatibility test is used to determine the incompatibility of the additional monomer with the elastomeric domain of the binder.

11. A flexographic photosensitive element which comprises a support; a layer of a photosensitive composition; said composition comprising
   (a) a styrene-butadiene-styrene block copolymer having thermoplastic styrene domains and elastomeric butadiene domains;
   (b) an initiator or initiating system activated by actinic radiation;
   (c) 1,6 hexanediol diacrylate as a first addition polymerizable ethylenically unsaturated monomer having some compatibility with both domains of the binder; and
   (d) dipentaerythritol monohydroxy pentaacrylate as an additional monomer which is substantially incompatible with the elastomeric domain of the binder, said monomer is added in an amount so that the ratio of the first monomer to the second monomer is in the range 1:4 to 4:1 based on total weight of monomer; and a flexible cover sheet.

* * * * *